United States Patent [19]

Miller

[11] Patent Number: 4,648,406

[45] Date of Patent: Mar. 10, 1987

[54] PHYSIOLOGICAL PRESSURE MEASURING SYSTEM

[75] Inventor: William Miller, Westport, Conn.

[73] Assignee: Michael Ebert, Mamaroneck, N.Y.

[21] Appl. No.: 230,640

[22] Filed: Feb. 2, 1981

[51] Int. Cl.$^4$ .............................................. A61B 5/02
[52] U.S. Cl. ................................... 128/674; 128/675; 128/748; 73/706; 73/716
[58] Field of Search ........... 128/672, 675, 748, 214 E, 128/214 R, 214 F; 73/731, 716, 701, 706

[56] References Cited

U.S. PATENT DOCUMENTS

| | | | |
|---|---|---|---|
| 3,648,687 | 3/1972 | Ramsey | 128/673 |
| 3,863,504 | 2/1975 | Borsanyi | 73/706 |
| 3,890,962 | 6/1975 | Ramsey | 128/673 |
| 3,980,082 | 9/1976 | Miller | 128/674 |
| 4,036,216 | 7/1977 | Ramsey | 128/675 |
| 4,206,761 | 6/1980 | Cosman | 128/748 X |
| 4,227,420 | 10/1980 | Lamadrid | 73/706 X |

OTHER PUBLICATIONS

"Moss Venous Pressure Monitor" USCI Corp., Glen Falls, N.Y., 1971.

Burch et al, Jour. A.M.A., vol. 123, No. 2, Sep. 11, 1943, pp. 91–92.

*Primary Examiner*—Kyle L. Howell
*Assistant Examiner*—John C. Hanley

*Attorney, Agent, or Firm*—Michael Ebert

[57] ABSTRACT

A physiological pressure measuring system usable in conjunction with an intravascular infusion line leading to a patient whose pressure is to be monitored. The system includes a detector having a transparent chamber interposed in the line and a flexible bulb mounted therein whose exterior is subjected to the fluid pressure in the chamber, the bulb interior communicating with a flexible pipe terminating in a hollow plug vented to the atmosphere whereby the bulb is caused to collapse when the infusion fluid pressure which reflects the physiolgial pressure is greater than atmospheric. Associated with the detector is a fluid pressure transducer yielding a signal as a function of the applied pressure, the transducer input port being in the form of a tubular jack adapted to telescopically receive the plug. When the plug is inserted in the jack, a seal is effected to create a closed air column which exerts pressure on the transducer. The effective length of the column depends on the relative axial position of the plug; and as the plug is advanced into the jack, the column is shortened to thereby compress the air entrapped therein. A point is reached in the course of advance when the column pressure matches the chamber fluid pressure, limited further advance resulting only in dilation of the bulb without any change in column pressure. The transducer senses the matching column pressure to provide the desired physiological pressure reading.

6 Claims, 6 Drawing Figures

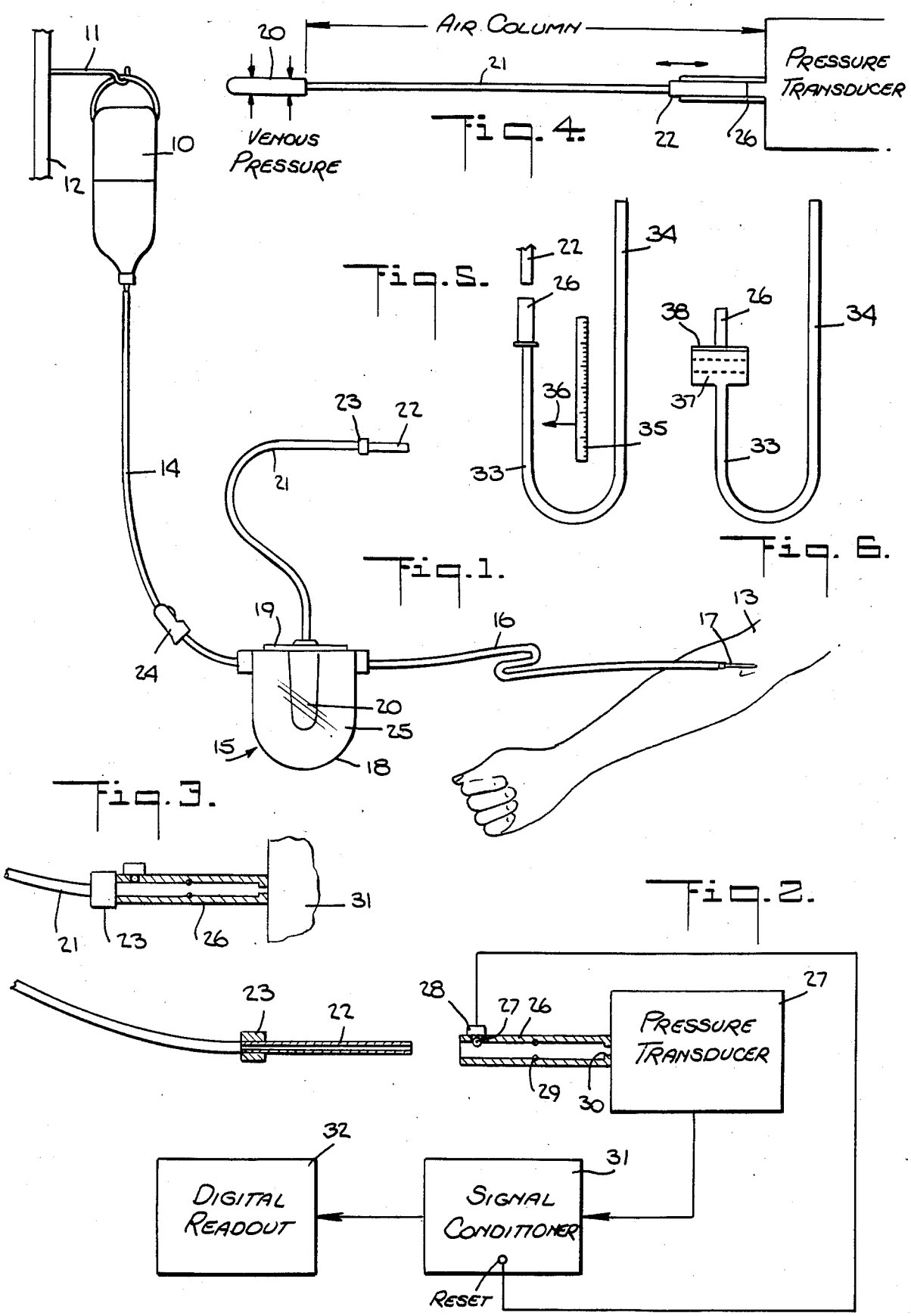

PHYSIOLOGICAL PRESSURE MEASURING SYSTEM

BACKGROUND OF INVENTION

This invention relates generally to the measurement of physiological pressure, and more particularly to an automated closed venous pressure measuring system.

While a system in accordance with the invention is capable of measuring physiological pressure such as arterial and venous blood pressures as well as intracranial, spinal, gastrointestinal, esophageal and intrauterine pressures, for purposes of explanation it shall be described mainly in the context of venous pressure measurement.

During many surgical procedures as well as in post-operative stages, it is now the usual practice to measure and record venous pressure. Venous pressure trends are a significant consideration in both diagnosis and prognosis. Moreover, such measurement is also important with respect to cardiovascular diseases; for an upward trend is one of the first signs of congestive heart failure.

The most commonly-used venous pressure measuring instrument is of the manometer type and includes a three-way stopcock and an intravenous needle to provide an arm puncture. The longitudinal passage in the stopcock connects the needle to a syringe, while its vertical outlet is coupled to the graduated manometer tube. In operation, blood is first drawn into the syringe which contains a sterile saline solution. After manipulation of the stopcock valve, the manometer tube is filled by expressing the mixture from the syringe. Thereafter, communication is restored between the manometer tube and the vein. This manometer, stop-cock combination may be used as part of an intravenous infusion apparatus, in which case the longitudinal passage in the stopcock connects the needle to the fluid supply, and the vertical outlet is coupled to the graduated manometer tube. During normal feeding, the fluid supply is connected to the needle, and the manometer tube is isolated. To read the pressure, the stopcock is first turned until the fluid supply is connected to the manometer (to flush the manometer), after which the stopcock is turned to connect the manometer to the needle. After the pressure is read, the needle is re-connected to the fluid supply.

The level to which liquid in the manometer falls upon reaching equilibrium is read directly from the tube scale, thereby providing a venous pressure reading. It will be recognized that the operating procedure for the manometer is somewhat complicated. Also, to obtain a correct reading, care must be exercised; and for this purpose the base of the manometer must be properly aligned with an appropriate point on the patient's body.

Venous pressure can vary through a relatively wide range: from a low of zero (or even negative values) relative to atmospheric pressure, to a high of 25 or 30 cm of water above atmospheric pressure. As a consequence, the conventional venous pressure instrument requires a fairly long manometer tube as well as associated apparatus that must be carefully assembled and properly supported. Because the upper end of the manometer tube is open to the atmosphere, the fluid is exposed and may be subject to bacterial contamination that is transmittable to the patient.

The intravenous (IV) infusion of various types of fluids to patients is a routine hospital procedure. In a standard IV system, a plastic bottle filled with a fluid such as glucose, serum or plasma, is supported at an elevated position to provide gravity flow through a flexible line whose end is coupled to a needle injected into a vein of the patient. In practice, there are many situations in which it is desirable to be able to infuse fluid into a patient or to take a venous pressure reading, using the same line for this purpose.

My prior patent (Miller), U.S. Pat. No. 3,980,082 (1976) discloses a venous pressure measuring instrument which is interposable in an intravenous infusion line or is usable separately therefrom to effect venous pressure measurement without exposing any of the fluid to the atmosphere, thereby avoiding the possibility of contamination. This venous pressure measuring instrument is interposed in a flexible infusion line leading to a patient, the downstream portion of the line functioning effectively as a manometer column, thereby dispensing with a supported manometer tube and the need to align the base of a remote manometer tube with a point on the patient's body.

The instrument disclosed in my prior patent is constituted by a transparent chamber interposed between an upstream line extending to the bottle containing the infusion fluid and a downstream line leading to a cannula. Visibly disposed within the chamber is a collapsible bulb that is vented to the atmosphere, the bulb being erect when the fluid pressure exerted on its exterior is not greater than atmospheric, the bulb collapsing when the fluid pressure is greater than atmospheric. Because the vent communicates only with the interior of the bulb, the fluid in the system is sealed from the atmosphere and contamination thereof is avoided.

In the infusion mode, fluid derived from the bottle and going to the patient passes through the chamber, and the resultant fluid pressure exerted in the bulb causes it to collapse. In the venous pressure mode, the upstream line is clamped to block flow from the bottle, as a result of which the fluid pressure then exerted on the bulb is a function both of venous pressure and the height of the chamber relative to the heart—the higher the chamber, the lower the fluid pressure.

By elevating the chamber to a point at which the fluid pressure exerted on the bulb is equal to atmospheric pressure, a balance or reference level is established, this balance level being indicated by the sudden erection of the bulb. Venous pressure is then determined by measuring the height of the chamber at the balance level relative to the heart, this measurement being made on a scale formed on the downstream line.

In another embodiment, the patented instrument is independent of an IV system, in which instance the chamber has no inlet but only a flexible line connection to the patient. The balance level is attained when the elevation of the chamber is such that at the interface of the air compressed in said line and the fluid derived from a body cavity, the pressures are equal, the body pressure being determined by measuring the height between the interface at the balance level and the body point.

Though a venous pressure measuring system of the type disclosed in my prior patent has distinct advantages over conventional instruments of the manometer type, it has certain practical drawbacks when used in hospitals. Because of the prevailing shortage of staff nurses, available personnel lack the time and patience necessary to take venous pressure readings which require up and down movement and observation of the degree of bulb collapse.

The need exists, therefore, for a venous pressure measuring system which is fool-proof and easy to operate, and which affords a direct readout, digital or otherwise, so that no particular care is demanded of the operator in order to obtain accurate and reliable measurements.

One prior attempt to provide an easily-operated system for monitoring physiological pressure is disclosed in the Minior et al. U.S. Pat. No. 4,185,641 assigned to the Hewlett-Packard Company and in the bulletins published by this company in connection with its model 1280C and model 1290A physiological pressure transducers.

In the Hewlett-Packard pressure measuring system, the fluid passing through a line leading to the patient flows into the hollow of a pressure dome closed by a flexible membrane, the membrane being distended as a function of fluid pressure. This membrane is maintained in intimate contact with the diaphragm of a pressure transducer to produce an electrical signal as a function of physiological pressure. As pressure varies, the membrane deflects the diaphragm accordingly and causes corresponding changes in the signal which provides a pressure indication.

The accuracy and reliability of the Hewlett-Packard instrument depends on the physical coupling between the dome membrane and the transducer diaphragm in intimate contact therewith. As pointed out in the Minior et al. patent, if the pressure dome is attached too lightly to the transducers, this will produce an offset in the fluid pressure signal; and if the dome is attached too loosely, the fluid pressure will not be fully transmitted to the transducer, again causing an erroneous reading.

SUMMARY OF INVENTION

In view of the foregoing, the main object of this invention is to provide a physiological measuring system which is interposable in an infusion line to effect pressure measurement without exposing any of the fluid to the atmosphere, thereby avoiding the possibility of contamination, the system requiring no up and down movement or other procedural complications to take a reading.

More particularly, an object of this invention is to provide a system which provides a digital readout and includes a detector interposed in a fluid line for sensing physiological pressure and a fluid pressure transducer coupled thereto by a quick-connect plug and jack assembly serving to impose a fluidic pressure on the transducer which corresponds to the physiological pressure being monitored.

A significant feature of the invention resides in its ease of operation. Thus in the case of venous pressure measurement, all that need be done is to insert the detector plug into the transducer jack and to push it inwardly to a stop position, this simple action providing the necessary fluidic link between the detector and the transducer and also automatically resetting the digital readout to provide an accurate reading.

Also an object of the invention is to provide a pressure-measuring system for use with an IV line in which a low-cost detector is integrated with the IV line and is disposable therewith, the associated transducer and digital display elements being non-disposable, so that a fresh and sterile IV line and detector combination may be used for each patient whose pressure is to be measured.

Yet another object of the invention is to provide a physiological pressure measuring system of uncomplicated construction that is relatively inexpensive to manufacture and which may be operated and read without difficulty.

Briefly stated, these objects are attained in a physiological pressure measuring system usable in conjunction with an intravascular infusion line leading to the patient whose pressure is to be measured. The system includes a detector having a transparent chamber interposed in the line and a flexible bulb mounted therein whose exterior is subjected to the pressure of fluid in the chamber, the bulb interior communicating with a flexible pipe terminating in a hollow plug vented to the atmosphere whereby the bulb is caused to collapse when the infusion fluid pressure which reflects the physiological pressure is greater than atmospheric.

Associated with the detector is a fluid pressure transducer yielding a signal as a function of the applied pressure, the transducer input port being in the form of a tubular jack adapted to telescopically receive the plug. When the plug is inserted in the jack, a seal is effected to create a closed air column which exerts pressure on the transducer. The effective length of the column depends on the relative axial position of the plug; and as the plug is advanced into the jack, the column is shortened to thereby compress the air entrapped therein. A point is reached in the course of plug advance when the column pressure matches the chamber fluid pressure, limited further advance resulting only in dilation of the bulb without any change in column pressure. The transducer senses the matching column pressure to provide the desired physiological pressure reading.

OUTLINE OF DRAWINGS

For a better understanding of the invention as well as other objects and further features thereof, reference is made to the following detailed description to be read in conjunction with the accompanying drawings, wherein:

FIG. 1 illustrates schematically an intravenous infusion system incorporating the detector of a venous pressure measuring system in accordance with the invention;

FIG. 2 shows the detector of the system in conjunction with the system transducer and digital readout;

FIG. 3 separately illustrates, in section, the plug and jack assembly for coupling the detector to the transducer, the plug being shown in its fully inserted condition;

FIG. 4 illustrates the variable air column created by the plug and jack assembly;

FIG. 5 schematically shows an embodiment of a measuring system in accordance with the invention using a manometer readout; and FIG. 6 shows an automated manometer readout.

DESCRIPTION OF INVENTION

Referring now to FIG. 1, there is shown an intravenous infusion system including an inverted bottle 10 containing a solution such as glucose. The bottle is suspended by means of a hook 11 extending from a stand 12. The IV system is conventional and may include a drip chamber and other elements not shown.

Because of gravity flow, the fluid in the bottle, which is elevated above a patient whose arm 13 is shown, passes down through a line 14 that is coupled to the inlet of the detector of the measuring system, generally designated by numeral 15. The IV system includes a line 16 connected to the outlet of the detector and coupled to a needle or cannula 17 which is injected in the vein of the patient.

Lines 14 and 16 are formed by flexible plastic tubing of the type used in standard IV sets. Since line 14 is on the upstream side of detector 15, it will hereafter be referred to as the upstream line; and since line 16 is on the downstream side, it will hereinafter be referred to as the downstream line. Installed on upstream line 14 is an on-off clamp 24 which, when closed, blocks flow from the bottle into venous pressure detector 15. In practice, one may dispense with the clamp and, when necessary, simply pinch the line with the fingers to interrupt flow.

Detector 15 is constituted by a transparent dome 18 of synthetic plastic material secured to a base 19 on which is mounted a flexible bulb 20 formed of a material non-reactive with the fluid. Dome 18 and base 19 define a chamber 25 through which the fluid passes, the exterior of the bulb being subjected to fluidic pressure. The interior of the bulb communicates with a flexible pipe 21 terminating in a hollow plug 22 provided with a handle ring 23, the bulb interior being thereby vented to the atmosphere.

Detector 15 is placed at the level of the heart of the patient (vena cava). Hence the pressure in the fluid surrounding the bulb is now the venous pressure of the patient being monitored. When the venous pressure exerted on the bulb exterior is greater than the interior (atmospheric) pressure on the bulb, the bulb flattens and collapses.

In the intravenous infusion mode, clamp 24 on upstream line 14 is open, thereby permitting flow of infusion fluid from bottle 10 and through line 14, chamber 25 and line 16 into the vein of the patient. Because of the column of fluid in the upstream line 14, the resultant fluid pressure within chamber 25 which is exerted on the exterior of bulb 20 is greater than the atmospheric pressure within the bulb. As a result, in the infusion mode, the bulb is flattened or collapsed and the passage through chamber 25 is unobstructed so that feeding of the fluid takes place in the same manner as would occur in the absence of the venous pressure measuring system. On the other hand, collapse of bulb 20 serves to seal off the end of pipe 21 coupled to the interior thereof.

If now one wishes to take a venous pressure reading, clamp 24 is closed to interrupt the supply of fluid to the patient. In the venous pressure mode, fluid pressure within chamber 25 is independent of the fluid column in upstream line 14. The pressure which now exists at all points in the system extending between the clamp position and the patient and including chamber 25 is a function of the intravascular fluid pressure in the patient.

To read this venous pressure, detector plug 22 is telescopically inserted into a tubular jack 26 serving as the input port of a pressure transducer 27, which may be any commercially-available transducer of good sensitivity suitable for the range of pressure involved. Thus quartz crystal, capacitive, inductive or any other type which translates pressure into proportional electrical values may be used. The transducer yields an analog electrical signal which is a function of the applied pressure.

The analog output of transducer 27 is fed to a signal conditioner 31 which digitizes the analog signal and acts to scale the signal to produce a digital output in appropriate pressure units. Signal conditioner 31 also provides a bias voltage so that its digital output will read zero when the transducer is exposed to atmospheric pressure. This digital output is applied to a digital display device 32 having a digital readout calibrated in terms of venous pressure.

When plug 22 is inserted into jack 26, its tip first engages the depressible actuator 27 of a microswitch 28. Activation of switch 28 produces a pulse which is applied to signal conditioner 31 to actuate its bias generator circuit therein to zero the system for atmospheric pressure and thereby reset the display.

As the plug is axially advanced into jack 26, it then engages an "0" ring 29 which acts to seal plug 22 and pipe 21 from the atmosphere to create a closed air column. As shown in FIG. 4, this column extends from the sealed mouth of the collapsed bulb 20 to the end of jack 26. Since plug 22 actuates microswitch 28 before it engages seal 29, zeroing will normally be completed in a fraction of a millisecond, well before the plug is sealed off. The length of the air column is determined by the fixed length of flexible pipe 21 and the variable length of the telescoping plug and jack assembly. Thus as the plug advances axially past the seal further into the jack, the air column is shortened, thereby compressing the air in the column. The resultant air pressure is exerted on the pressure transducer.

As the plug continues to advance in the jack toward a stop 30, the air pressure in the column builds up until a point is reached where the pressure in the column exactly matches the existing fluid pressure in the detector chamber that reflects venous pressure and is applied to the exterior of bulb 22.

Beyond this point any further inward advance of plug 22, though shortening the air column, will not give rise to an increase in column pressure; for air pressure exceeding the matching point is relieved by bulb 20 which now proceeds to dilate to accommodate the air displaced by the shortened column. In other words, before the matching point, the column is effectively sealed at one end by the collapsed bulb, this seal being ruptured when pressed beyond this point, to cause distension of the bulb.

The parameters of the arrangement including the maximum volume of bulb 20 are such as provide adequate relief for the full range of venous pressures, so that at no time is the bulb fully dilated. Since venous pressure is usually in the range of zero to approximately 1% of ambient, the plug should advance beyond the "0" ring until it displaces a volume of 1% trapped volume plus about one-half of the volume of the fully-distended bulb, the stop position being determined by these factors.

Thus all an operator need do is to push plug 22 into jack 26 until it reaches the stop therein. This action brings about zero referencing and pressure equalization automatically.

In practice, the digital display can be blanked out at will, and this can be controlled by a single switch. Thus microswitch 28 can also be used to keep the display dark until such time as plug 22 is inserted in the jack. Furthermore, the digital portion of the display can be controlled independently of the (+) and (−) indications, and these indications can be left on all the time to show that the electronics is ready, the digits appearing only when the detector plug is inserted in the transducer jack.

In practice, detector 15 is integrated with the IV set and may be disposed therewith after use. Since the detector consists of low-cost plastic components which may be fabricated at low cost, the addition of the detector to the IV set does not add materially to the cost thereof. The presence of the detector does not interfere with the normal operation of the IV set, for fluid flows without obstruction through the detector chamber.

While there has been shown and described a preferred embodiment of physiological pressure measuring system in accordance with the invention, it will be appreciated that many changes and modifications may be made therein without, however, departing from the essential spirit thereof. For example, instead of depending on a telescoping plug and jack arrangement to bring about a match between the pressure of the trapped air imposed on the transducer and the fluid pressure imposed on the bulb exterior, one may provide a hand-operated pump included in the pipe leading from the bulb interior to the transducer for this purpose.

Instead of sensing the plug-jack assembly air column pressure which is proportional to physiological pressure by means of a pressure transducer and associated electronic equipment, the air column pressure may be detected by a standard water-filled manometer, as shown in FIG. 5. The short left column 33 of this manometer has its inlet directly coupled to hollow jack 26, the U-shaped manometer tube having a long right column 34 exposed to the atmosphere.

This manometer may be mounted at any level and, therefore, for convenience, may be supported on a suitable stand at eye level. After plug 22 is inserted in jack 26 to seal off the atmosphere, the entrapped air pressure then applied to the manometer representing the physiological pressure being monitored. This pressure may be read as a difference in height between the left and right columns of the manometer. To facilitate readout, a sliding indicator 35 having a scale therein is movable in a vertical path between the left and right columns, the indicator having a pointer 36 which runs along the left column 33. By aligning pointer 36 with the level of water in the left column, one can then read the height of the water in the right column on the indicator scale.

The advantage of using a manometer in conjunction with the jack and plug assembly is that this is a generally-available, non-electronic instrument for pressure measurement. The drawback to using a manometer in a conventional manner for physiological pressure measurement is that, because it is directly coupled to the IV system, it is ordinarily necessary to dispose of the manometer after testing a patient. But with the present arrangement, the manometer is isolated by the jack and plug assembly from contaminants, and this relatively costly instrument may be permanently installed for repeated testing. In practice, the manometer water may be dyed to facilitate readout.

FIG. 6 shows a modified manometer detector to automate the readout. To this end, the left column 33 of the manometer is terminated in a reservoir section 37 of enlarged diameter enclosed by a cap 38 into which jack 26 is fitted. Thus by inserting plug 22 into the jack to seal off the atmosphere in the manner previously explained, the entrapped air pressure applied to the head of water in section 37 reflects the physiological pressure being monitored.

The normal water level in section 37 at atmospheric pressure is such that it lies in line with the zero mark on the graduated right column 34 of the manometer. Then when the plug is inserted in jack 26 and an above-atmospheric pressure is applied by X centimeters of water will cause the water in the right column to rise by approximately X centimeters. However, water in the left column will only drop by $X \cdot (d_1/d_2)^2$, wherein $d_1$ is the diameter of the right column and $d_2$ is the diameter of the left column.

Inasmuch as the rise in right column 34 is much greater than the drop in height in left column 33 in response to an applied pressure by a factor of at least 100, the resultant right column rise is almost exactly proportional to applied pressure, even though it does not precisely reflect this pressure. For example, if the diameter of enlarged section 37 is one inch and that of right column 34 is 1/16 inch, then the height of water in right column 34 will be equal to the pressure change within one part in 256. Thus the accuracy of the manometer in this arrangement is more than adequate for physiological pressure measurement.

I claim:

1. A physiological pressure measuring system comprising:
   (A) an intravascular infusion set having a line carrying fluid to a patient whose pressure is to be monitored:
   (B) a detector having a transparent chamber interposed in the line whereby the fluid carried to the patient flows through the chamber, and a flexible bulb mounted in the chamber, the exterior of the bulb being subjected to the pressure of the fluid in the chamber, the interior of the bulb communicating with a flexible pipe terminating in a hollow detector plug initially vented to the atmosphere whereby the bulb is collapsed when the chamber fluid pressure is greater than atmospheric;
   (C) a transducer producing an analog signal as a function of applied pressure; and
   (D) an input port coupled to said transducer to apply pressure thereto, said input port being defined by a tubular transducer jack adapted to telescopically receive and seal from the atmosphere said hollow detector plug which is axially advanceable into said transducer jack such that when a pressure reading is to be taken, an operator then inserts and axially advances the detector plug into said transducer jack to create in said pipe an air column whose effective length is determined by the length of the pipe and the variable length of the telescoping plug and jack and which is closed by the collapsed bulb to entrap the air therein, the effective length of the air column therefore depending on the axial position of the detector plug so that as the detector plug is advanced by the operator into the transducer jack to shorten the column, the entrapped air then is compressed to exert a pressure on the transducer, the parameters of the pipe and the telescoping plug and jack relative to the full range of pressures encountered in patients being such that a point is reached in the course of said advance where the air pressure in the column matches the pressure of fluid in the chamber, beyond which point further advance of the detector plug results in partial dilation of the collapsed bulb to relieve any increase in the column air pressure whereby the matching column pressure sensed by the transducer is maintained to provide the desired pressure reading.

2. A system as set forth in claim 1, further including means to convert the analog signal to a digital value, and display means to present said digital value.

3. A system as set forth in claim 1, wherein said jack includes a microswitch actuator adjacent the opening thereof, whereby when said plug is inserted, the switch is actuated thereby to produce a pulse for resetting the digital display means.

4. A system as set forth in claim 3, further including an "0" ring in said jack at a position therein beyond said actuator to seal off the plug from the atmosphere after the switch is actuated.

5. A system as set forth in claim 4, wherein said jack further includes a stop at a position therein beyond said ring to arrest any further advance of the plug.

6. A system as set forth in claim 1, wherein said infusion set includes an insertable bottle for said fluid coupled to said line and a clamp in said line.

* * * * *